Figure 5:
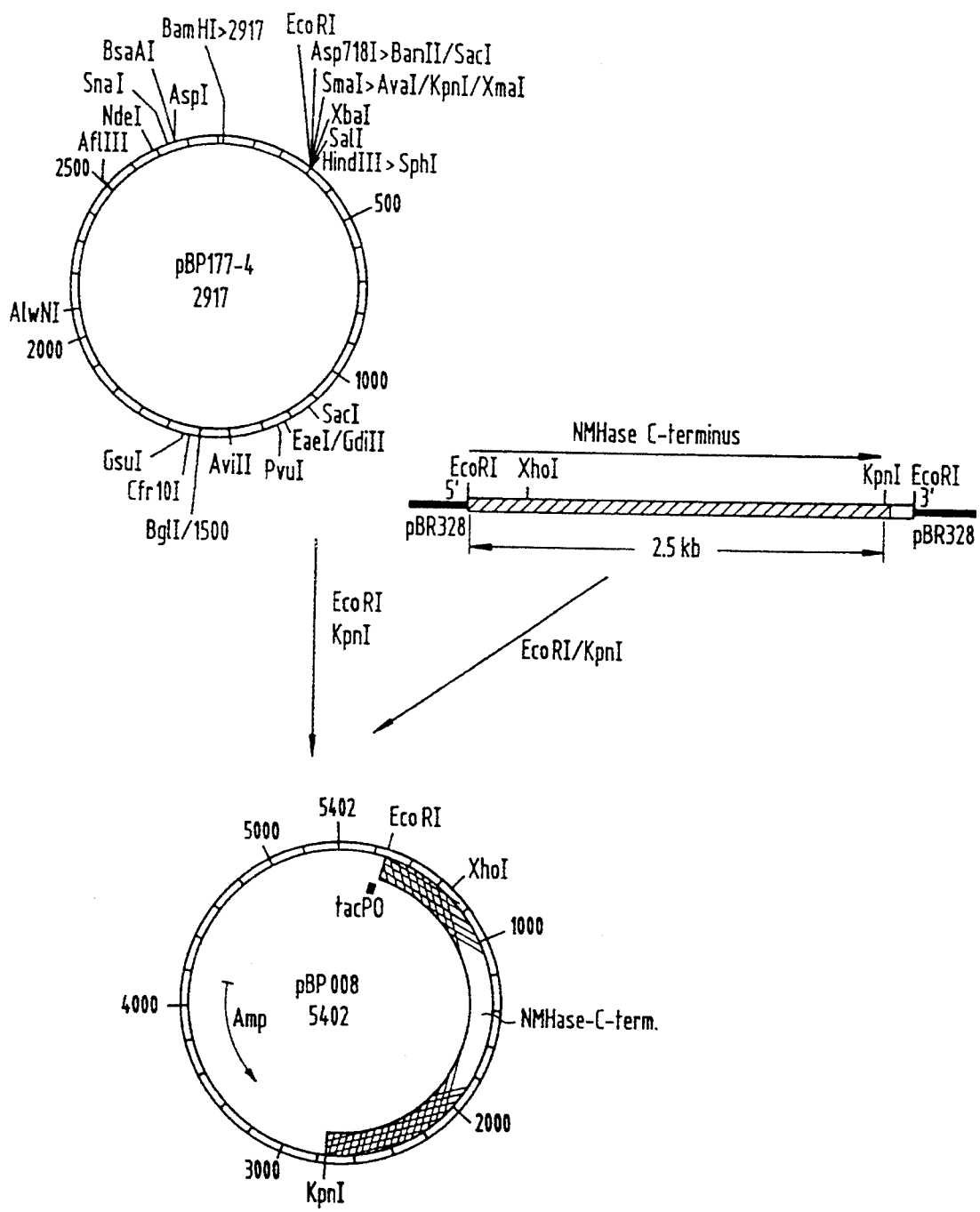

United States Patent [19]

Schumacher et al.

[11] Patent Number: 5,432,070
[45] Date of Patent: Jul. 11, 1995

[54] CLONED N-METHYLHYDANTOINASE

[75] Inventors: Günther Schumacher, Bernried; Helmut Burtscher, Habach; Hans Möllering, Tutzing, all of Germany

[73] Assignee: Boehringer Mannheim GmbH, Germany

[21] Appl. No.: 258,614

[22] Filed: Jun. 10, 1994

Related U.S. Application Data

[60] Continuation of Ser. No. 21,856, Feb. 24, 1993, abandoned, which is a division of Ser. No. 727,814, Jul. 8, 1991, Pat. No. 5,213,969.

[30] Foreign Application Priority Data

Jul. 6, 1990 [DE] Germany ............ 40 21 571.7

[51] Int. Cl.$^6$ ............ C12Q 1/34; C12N 9/14; C12N 9/86; C12N 9/96
[52] U.S. Cl. ............ 435/188; 435/195; 435/231; 435/18
[58] Field of Search ............ 435/18, 188, 195, 231

[56] References Cited

U.S. PATENT DOCUMENTS 4,816,393 3/1989 Siedel et al. ............ 435/18

FOREIGN PATENT DOCUMENTS

| 0437254A2 | 7/1791 | European Pat. Off. |
| 0154269 | 4/2287 | European Pat. Off. |
| 0219034 | 4/2287 | European Pat. Off. |
| WO88/09373 | 12/1988 | Germany |

OTHER PUBLICATIONS

Berger et al "Guide to Molecular Cloning Techniques", Methods in Enzymology, vol. 152, Academic Press Inc. (1987).
Suggs et al. Proc. Nat. Acad. Sci. USA vol. 78, 6613–6617 (1981).
Young et al. Proc. Nat. Acad. Sci., USA vol. 80, 1194–1198 (1983).
Biological Abstracts, vol. 86, 1988, No. 45041.

Primary Examiner—Robert A. Wax
Assistant Examiner—Gabriele E. Bugaisky
Attorney, Agent, or Firm—Nikaido, Marmelstein, Murray & Oram

[57] ABSTRACT

The invention concerns a DNA which codes for a protein with N-methylhydantoinase activity and which has
1.) the nucleic acid sequence shown in FIG. (1),
2.) a sequence corresponding to it within the scope of the degeneracy of the genetic code or
(3) a sequence which hybridizes with a sequence from (1) or/and (2) under stringent conditions.

Furthermore the invention also concerns a recombinant vector which contains a DNA according to the present invention, a cell which is transformed with a vector according to the present invention as well as a process for producing a recombinant protein with NMHase activity.

1 Claim, 7 Drawing Sheets

Fig.1
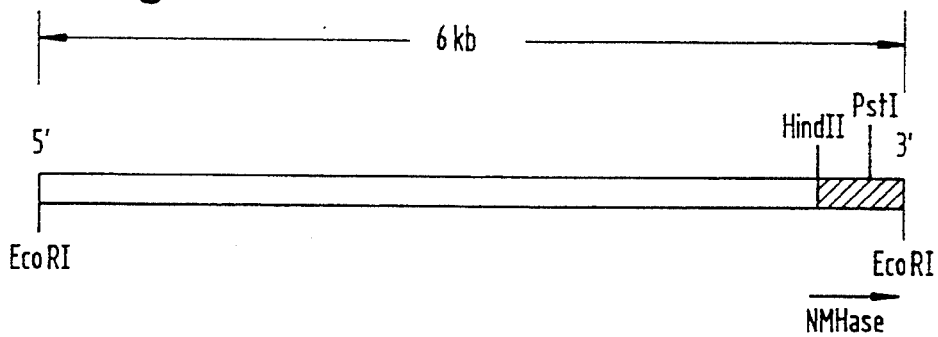
Fig.2
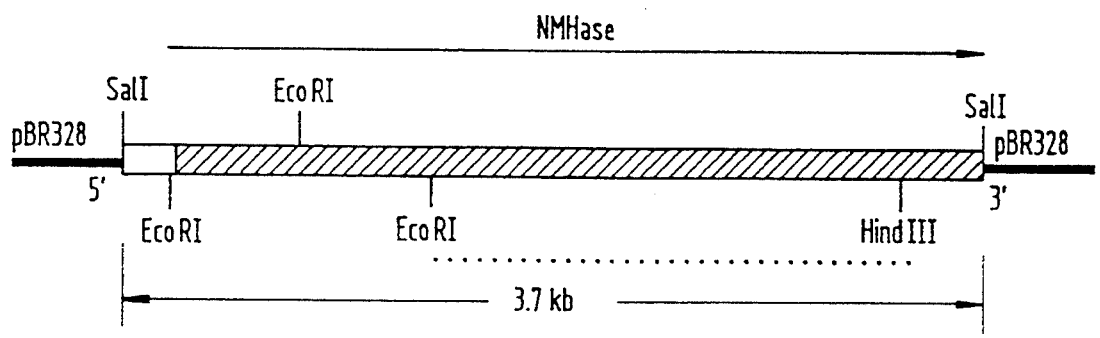
Fig.3
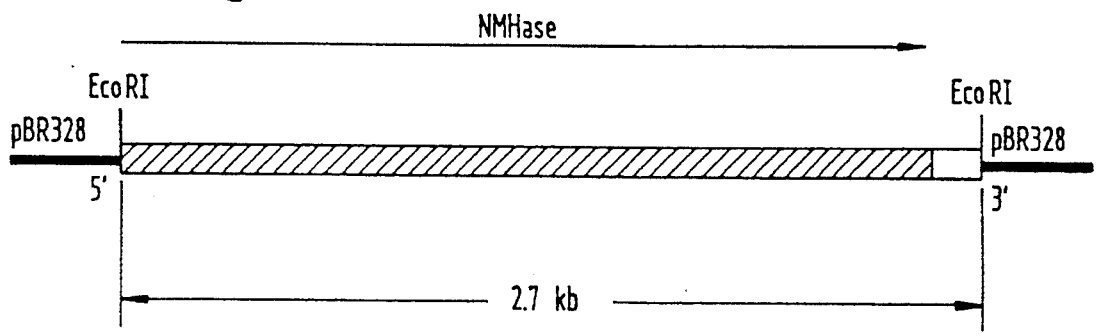
Fig.4
Linker Fragment
```
5'-AATTCTTATGAAGCGCATCGGAGTAGACGT-3'
   ||||||||||||||||||||||||||
 3'-GAATACTTCGCGTAGCCTCATC-5'
```

CLONED N-METHYLHYDANTOINASE

This application is a continuation of application Ser. No. 08/021,856, filed Feb. 24, 1993, abandoned, which is a Rule 60 Divisional of U.S. Ser. No. 07/727,814, filed Jul. 8, 1991, now U.S. Pat. No. 5,213,969.

The enzyme N-methylhydantoinase (NMHase) is required for the determination of the content of creatinine in liquids. The creatinine level is an important parameter for kidney diagnostics. Annually about one thousand million tests are carried out worldwide. Therefore the provision of the enzyme NMHase at a low cost, as well as the possibility of an unproblematic fermentation are basic requirements for the provision of diagnostic kits for the determination of creatinine. The molecular weight of NMHase is 125 kD in an SDS gel. The specific activity is 2 U/mg, the $K_M$ for N-methylhydantoin is $2 \times 10^{-5}$ mol/l. NMHase is usually isolated from Arthrobacter. However, this process has drawbacks which are related to the microorganism used.

Improved methods of isolation must therefore be developed in order to provide larger amounts of NMHase. This was also the object of the present invention.

The object according to the present invention could be achieved by cloning the gene coding for the NMHase from Arthrobacter and expressing it in a suitable host organism.

The present invention thus provides a DNA which contains (1) the nucleic acid sequence shown in SEQ ID NO: 1, (2) a sequence corresponding to it within the scope of the degeneracy of the genetic code or (3) a sequence which hybridizes with the sequences from (1) or/and (2) under stringent hybridization conditions and which codes for a protein with NMHase activity. In this connection reference is made to Maniatis et al. (1982) "Molecular Cloning. A laboratory manual", Cold Spring Harbor Laboratory, New York, for the meaning of hybridization under stringent conditions in the present invention.

The DNA according to the present invention codes for a protein with 1288 amino acids whose sequence is shown in SEQ ID NO: 2. The present invention thus also encompasses a protein with NMHase activity and with the amino acid sequence shown in SEQ ID NO: 2 or an amino acid sequence derived therefrom, which is obtained by genetic engineering methods e.g. by expression in a heterologous organism i.e. in an organism in which the gene coding for the protein according to the present invention does not originally occur. On the other hand, it is also possible to achieve an improved expression of the NMHase gene by introducing one or several copies of the DNA according to the present invention into an organism in which a DNA according to the present invention is present.

The present invention in addition provides a recombinant vector which contains one or several copies of a DNA according to the present invention. A recombinant vector according to the present invention can be a vector which is suitable for protein expression in prokaryotic or eukaryotic organisms. It is preferably a prokaryotic vector.

A recombinant vector according to the present invention can be a vector which is present extrachromosomally in a host cell (e.g. plasmid) or is integrated into the genome of the host (e.g. bacteriophage lambda). The recombinant vector according to the present invention is preferably a plasmid. A suitable plasmid according to the present invention is e.g. the plasmid pBP010.

The DNA which codes for a protein with NMHase activity is located on a recombinant vector according to the present invention and is preferably under the control of a regulatable promoter, which means that an expression of the DNA according to the present invention can be suppressed for example by a repressor and only takes place when the regulatable promoter is specifically induced. This induction can for example take place by a change in temperature or by addition of a chemical inducer (e.g. IPTG for lac promoter derivatives). In a particular preferred embodiment of the present invention the regulatable promoter which is intended to control the NMHase gene is the mgl promoter from *Salmonella typhimurium* (WO 88/09373) which can be regulated by means of catabolite repression by sugars such as e.g. glucose and fructose.

A suitable vector according to the present invention for the expression of NMHase in gram-negative bacteria, in particular *E. coli*, is e.g. the plasmid pBP006. In order to construct pBP006, a DNA fragment, which contains the sequence of the mgl promoter from *Salmonella typhimurium*, was isolated from the plasmid pPZ07-mgl-lac (described in WO 88/09373, FIG. 8) and cloned upstream of a DNA fragment which contains the sequence coding for the NMHase gene from Arthrobacter without its own promoter.

The present invention also provides a cell which is transformed with a DNA according to the present invention or with a recombinant vector according to the present invention. This cell is preferably a bacterial cell, particularly preferably an *E. coli* cell.

The DNA according to the present invention is obtained by cloning the NMHase gene. Chromosomal DNA from Arthrobacter was isolated for this by conventional methods and cleaved with suitable restriction enzymes. A gene bank of these DNA fragments was set up in *E. coli*. However, a cloning of the NMHase gene in the usual manner (screening the gene bank with oligonucleotide probes and selection of the clones by means of NMHase activity) did not succeed. In fact no NMHase activity was found in any of the Arthrobacter DNA fragments used when cloned in *E. coli*. This finding was surprising since a DNA fragment of the correct length with a start and stop codon could be identified on the basis of hybridization with the oligonucleotide probe. An NMHase activity could only be detected when cloning DNA fragments on which the native NMHase promoter was absent.

The invention also provides a process for the production of a protein with NMHase activity in which a cell is transformed with a DNA according to the present invention or with a recombinant vector according to the present invention, the transformed cells are cultured in a suitable medium and the protein is isolated from the medium or the cells.

*E. coli* bacteria are preferably used as the host organism for the process according to the present invention. In this connection it is, however, advantageous to culture the transformed cells under suboptimal growth conditions. Suboptimal growth conditions are for example understood as a reduced temperature during the incubation (30° C. or less), a reduction of the oxygen transfer or/and the use of a minimal medium (i.e. a medium which contains certain essential nutrients for the cultured organism in limiting concentrations).

Thus for instance the culture conditions in a process for the isolation of NMHase from *E. coli*, in which a recombinant vector is used which contains the NMHase gene under the control of the tac promoter, is a minimal medium, an incubation temperature of less than 30° C. and an incomplete induction of the tac promoter with 0.8% lactose.

The particularly preferred expression of the NMHase gene under the control of the mgl promoter of *Salmonella typhimurium* preferably also takes place at an incubation temperature of 30° C. or less, which if desired is coupled with an additional reduction of the oxygen transfer so that the NMHase formed does not accumulate in an inactive form as precipitation bodies. The mgl promoter is regulated by catabolite repression (U.S. patent application Ser. No. 300,357).

In general it is preferred for the process according to the present invention that the induction of the regulatable promoter used in each case is only carried out incompletely which also contributes to a reduced formation of precipitation bodies.

In addition it is particularly preferred for the process according to the present invention that, for the purpose of stabilization and preferably during the isolation of the NMHase from the transformed cells or the medium, the protein is incubated with the enzyme substrate N-methylhydantoin. Surprisingly the stability of the recombinant NMHase obtained by the process according to the present invention can be substantially increased by the presence of an amount of approximately 3.8 nmol N-methylhydantoin per unit (U) of the enzyme. For this the enzyme is incubated with a N-methylhydantoin solution, preferably at a concentration of 1 to 100 mmol/l, particularly preferably of 10 to 70 mmol/l, most preferably of 50 mmol/l. In this incubation step it is advantageous to increase the temperature to e.g. 55° C. It is especially surprising that the presence of its own substrate stabilizes the enzyme and that at the same time the enzymatic reaction of the recombinant enzyme does not interfere.

The present invention also encompasses a reagent for the determination of the content of creatinine in liquids which contains a protein obtained according to a process according to the present invention in addition to the usual constituents.

The following examples are intended to further elucidate the invention in conjunction with the sequence protocols and FIGS. 1 to 10.

Figure 6:
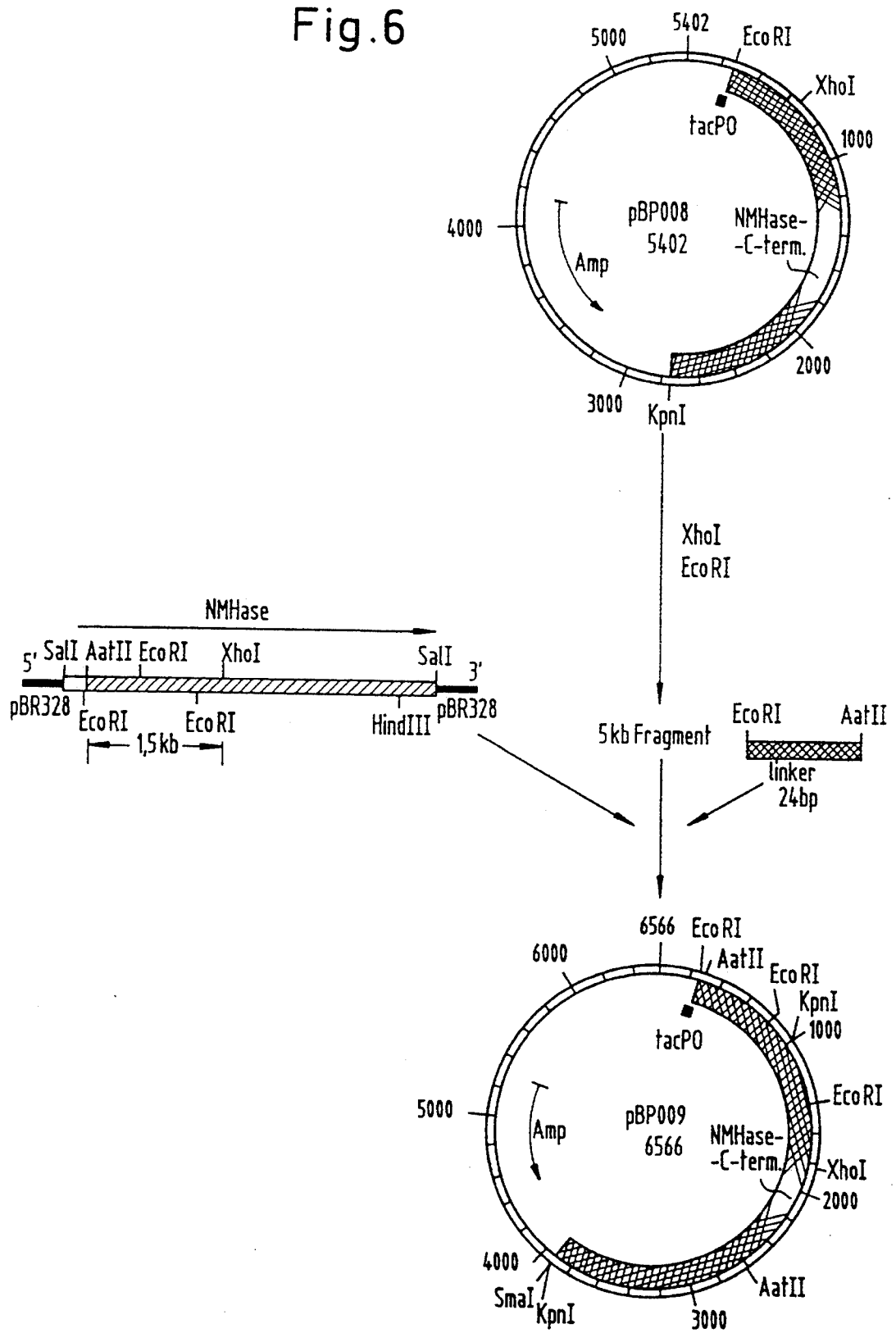
Figure 7:
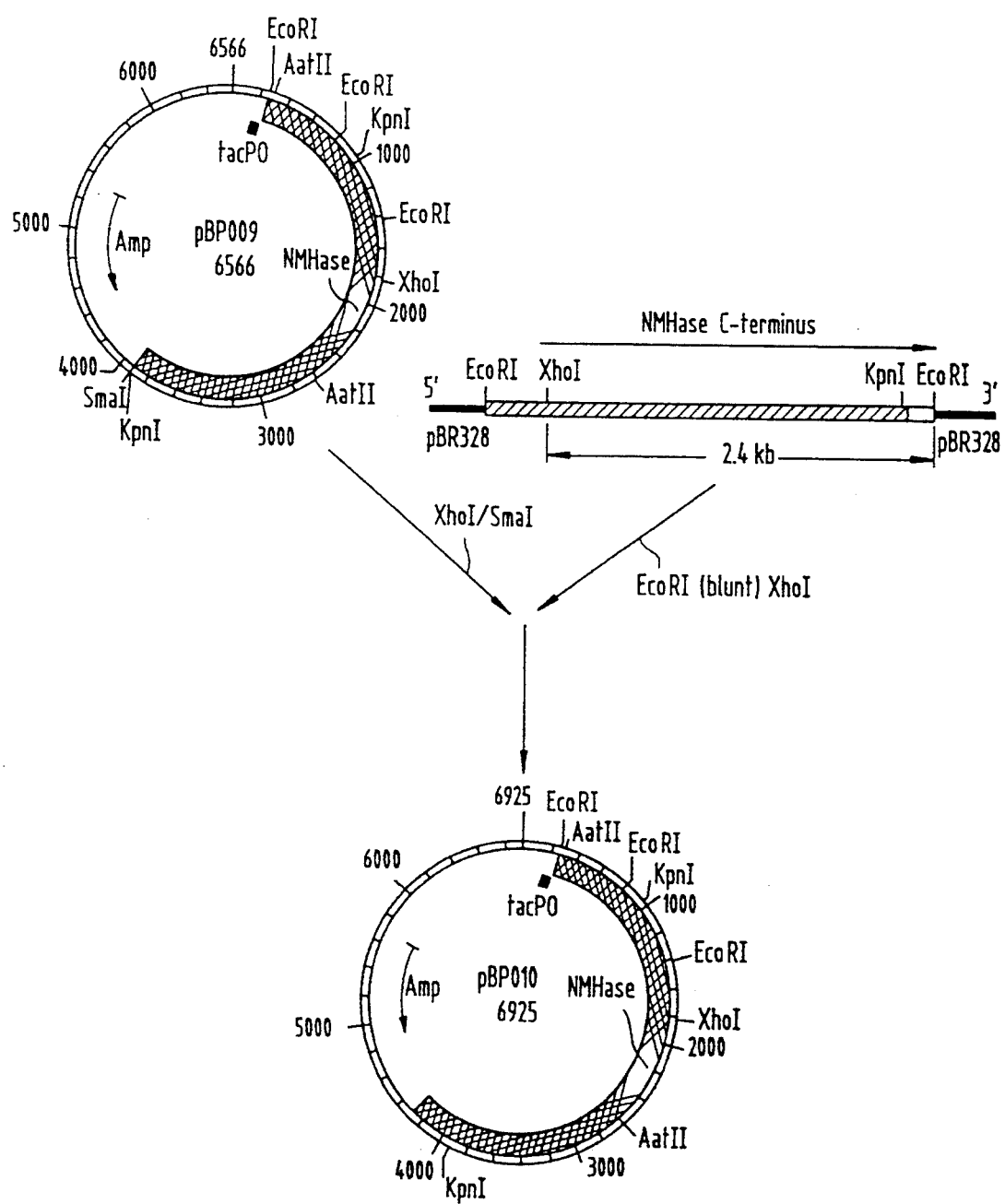
Figure 8:
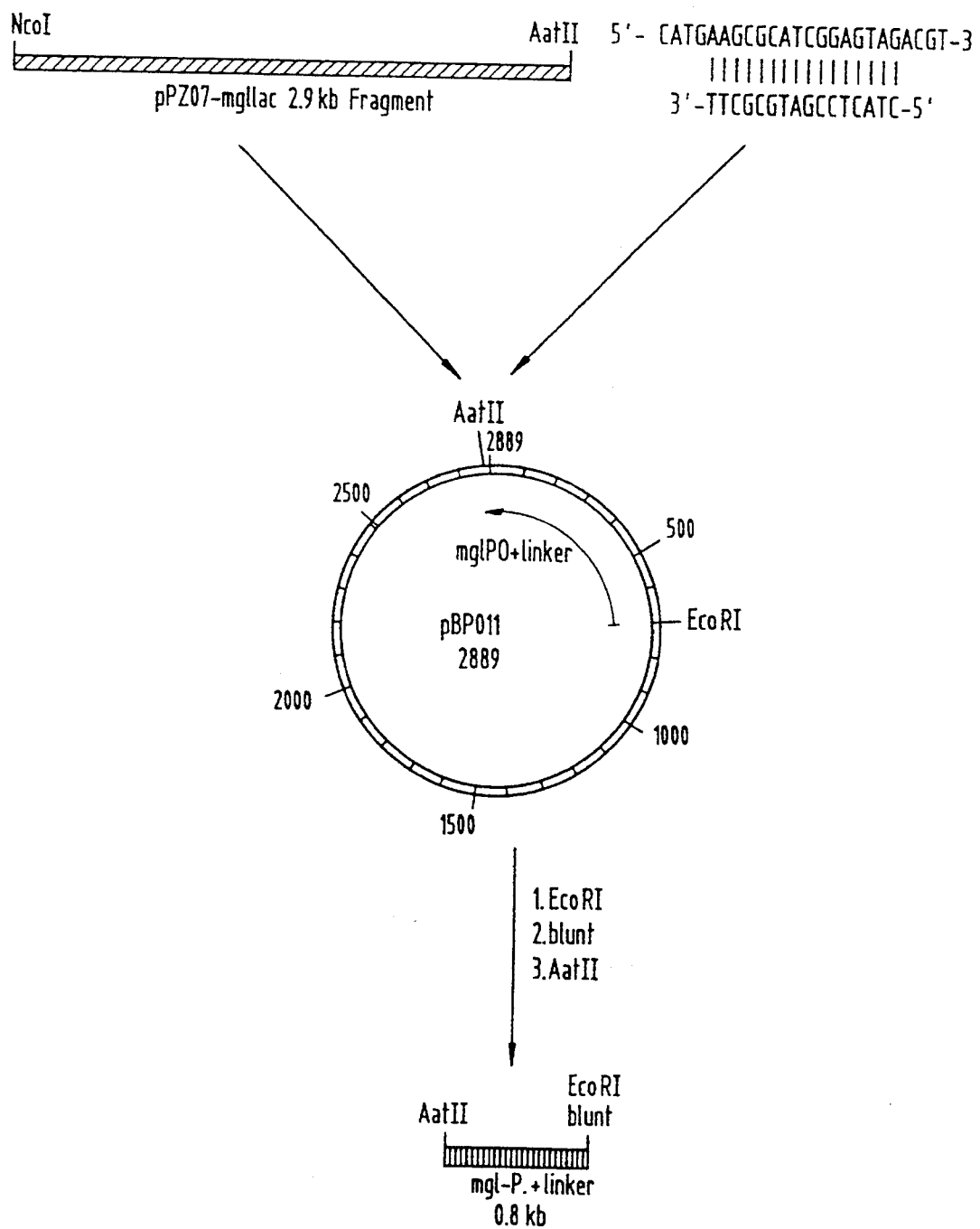
Figure 9:
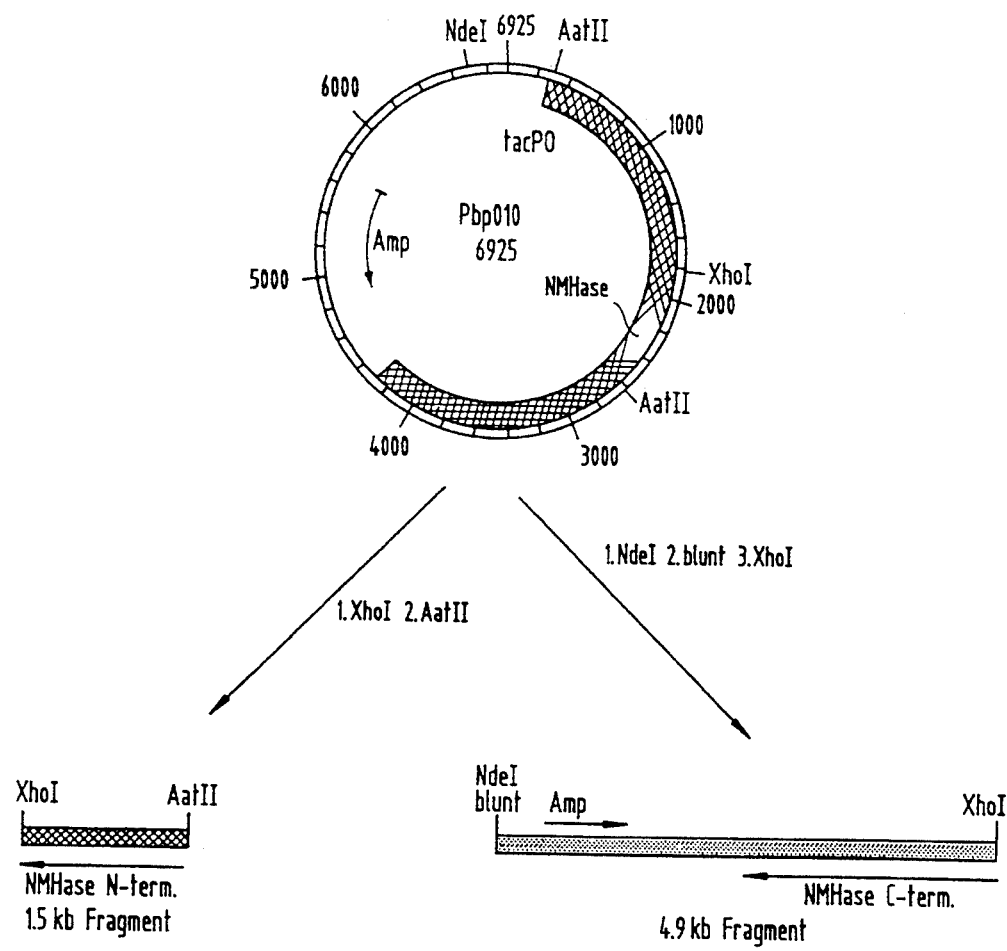
Figure 10:
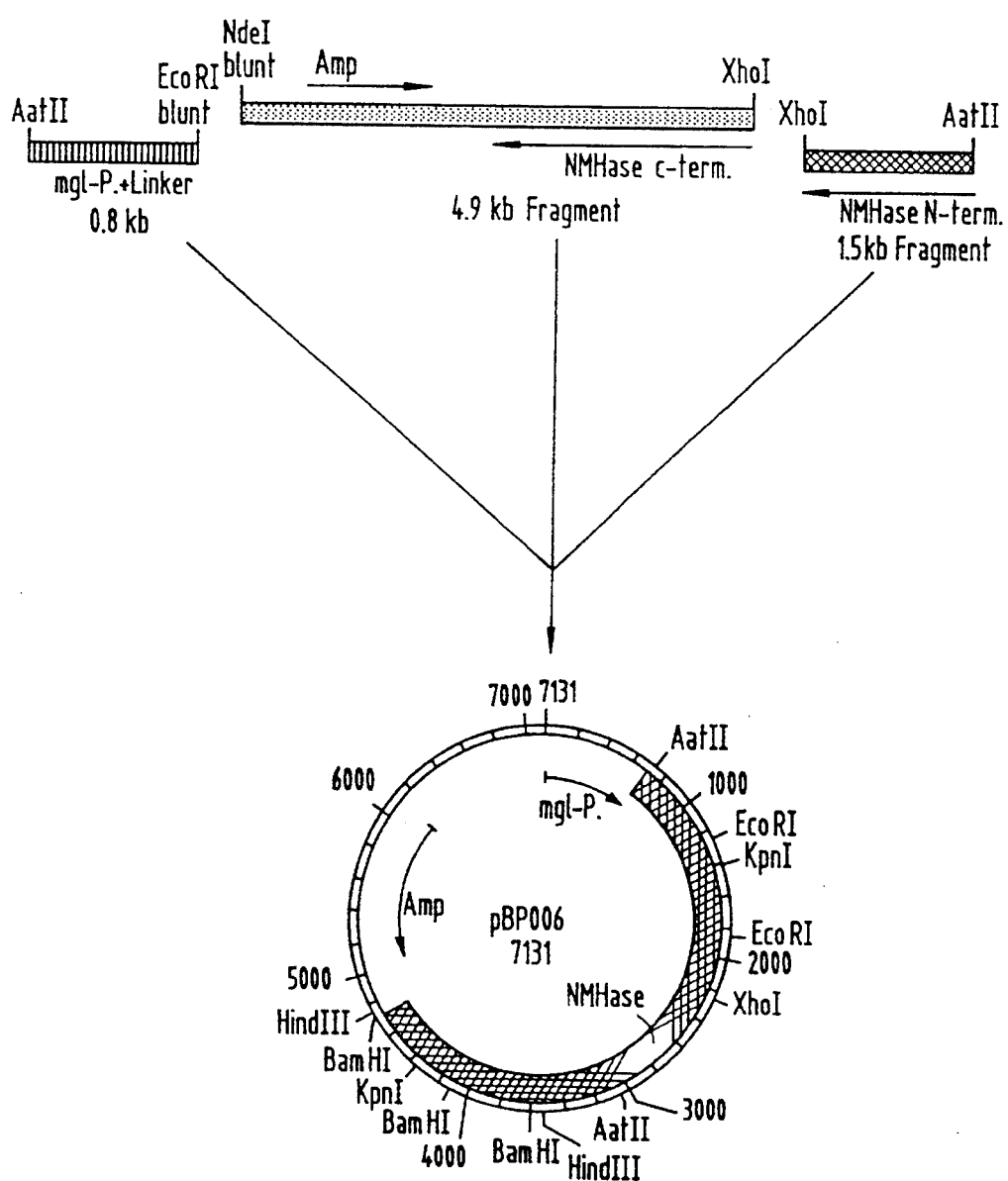

SEQ ID NO: 1 shows the DNA sequence of the NMHase gene,

SEQ ID NO: 2 shows the amino acid sequence of the NMHase derived therefrom,

FIG. 1 shows a 6 kb long EcoRI fragment from Arthrobacter with a ca.0.6 kb long fragment of the NMHase gene, FIG. 2 shows a 3.7 kb long SalI fragment from Arthrobacter with a 3.0 kb long region coding for the NMHase gene, FIG. 3 shows the 3′-terminal region of the NMHase gene, FIG. 4 shows an EcoRI/AatII linker, FIG. 5 shows the construction of the plasmid pBP008, FIG. 6 shows the construction of the plasmid pBP009, FIG. 7 shows the construction of the NMHase expression plasmid pBP010, FIG. 8 shows the construction of the plasmid pBP011 with the mgl promoter from *Salmonella typhimurium*, FIG. 9 shows the isolation of fragments of the NMHase gene from pBP010, FIG. 10 shows the construction of the NMHase expression plasmid pBP006.

EXAMPLE 1

Cloning of the NMHase

DNA was isolated according to the usual methods from Arthrobacter spec. DSM 2563 (J. Marmur—A procedure for the isolation of deoxyribonucleic acid from microorganisms, J.Mol.Biol. 3, 208–218 (1961); S. Visuvanathan et al.—Simple enzymic method for isolation of DNA from diverse bacteria, Journal of Microbiological Methods 10, 59–64 (1989)) and cleaved with the restriction enzymes EcoRI or HindIII. Bacteriophage λgt10 (Boehringer Mannheim GmbH) was used as the cloning vector for the Arthrobacter DNA. The Arthrobacter DNA was cloned in λgt10 according to the instructions of the producer.

The Arthrobacter gene bank obtained was screened with an oligonucleotide probe which was derived from a partial peptide sequence of NMHase.

Partial peptide sequence of NMHase (SEQ ID: 3): Met Lys Arg Ile Gly Val Asp Val Gly Gly Thr Phe Thr Asp Leu Tyr Phe.

The following oligonucleotide probes were derived from this partial peptide sequence:
1. ATG AA(G/A) (C/A)G(G/A) AT(A/C/T) GG(G/A/T/C) GT (SEQ ID: 4)
2. ATG AA(G/A) (C/A)G(T/C) AT(A/C/T) GG(G/A/T/C) GT (SEQ ID: 5)
3. ATG AAG CGC ATC GGC GTG GAC GTG GGC GGC ACG TTC ACC GAT CTG TAC TT (SEQ ID: 6)

Using these oligonucleotide probes a 6 kb long EcoRI fragment was found in the λgt10 gene bank which contains a part of the NMHase gene (ca. 0.6 kb) (FIG. 1).

A part of this fragment (ca. 300 bp between the cleavage sites PstI and EcoRI) was radioactively labelled with $^{32}P$. Subsequently Arthrobacter DNA was cleaved with the restriction enzyme SalI, separated on an agarose gel and hybridized in a Southern Blot with the radioactively labelled DNA fragment. The hybridizing DNA region was cut out of the agarose gel and cloned into the SalI restriction cleavage site of the tetracycline resistance gene of pBR328 (Boehringer Mannheim GmbH).

An examination of *E. coli* cells transformed with this plasmid resulted in a 3.7 kb long DNA fragment which contains a 3.0 kb long region of the NMHase gene (FIG. 2).

The EcoRI/Hind III fragment from this insertion which is marked by a dotted line was labelled with digoxigenin (Boehringer Mannheim, Dig Kit). The λgt10 gene bank already mentioned above was again screened with this probe whereby a 2.7 kb piece was found which contains the 3′-terminal region of the NMHase gene (FIG. 1). This DNA fragment was also cloned into the vector pBR328.

EXAMPLE 2

Expression of NMHase 2.1 Conventional methods

The 3.7 kb long SalI fragment (FIG. 2) was cloned into the commercially available vector pUC19 (Boehringer Mannheim GmbH). Subsequently the NMHase gene was completed by cloning in the EcoRI fragment of FIG. 3. However, such a construct does not lead to the expression of active NMHase.

An attempt to achieve expression of this construct by cloning under the control of an inducible tac promoter and inducing the tac promoter in the usual way (incubation at 37° C., complete medium and complete induction of the tac promoter) also failed. For this the plasmid pKK177-3 (DSM 3062) was cleaved with EcoRI and HindIII and ligated with a polylinker cut out of pUC19 by means of EcoRI and HindIII. The plasmid which forms was denoted pBP177-4. Subsequently the plasmid pBP177-4 was cleaved with EcoRI and KpnI and combined with a 2.5 kb C-terminal NMHase fragment (also cleaved with EcoRI and KpnI) to form the plasmid pBP008 (FIG. 5).

The plasmid pBP008 was cleaved with the enzymes XhoI and EcoRI and the resulting large (5 kb) fragment was combined with a 1.5 kb fragment from the NMHase N-terminus which has the end-cleavage sites AatII and XhoI and with an EcoRI-AatII linker (see FIG. 4) to form plasmid pBP009 (FIG. 6). A protein whose molecular weight approximately corresponds to that of NMHase was expressed in *E. coli* cells which were transformed with this plasmid. However, no enzymatic activity could be detected.

2.2 Process according to the present invention First a C-terminal extension of the NMHase was carried out. The plasmid pBP009 (FIG. 6) was cleaved for this with the enzymes XhoI and SmaI and a resulting 5.5 kb DNA fragment is isolated which contains the tac promoter, the N-terminal region of NMHase and the ampicillin resistance gene. This fragment was combined with a C-terminal NMHase fragment from pBR328 which has the end-cleavage sites EcoRI (blunt ends by treatment with Klenow polymerase) and XhoI to form plasmid pBP010 (FIG. 7), pBP010 is able to express NMHase.

In the next step the NMHase gene was brought under the control of the mgl promoter from *Salmonella typhimurium* (described in WO 88/09373). For this the plasmid pPZ07/mgllac (described in WO 88/09373) was cleaved with the enzymes NcoI and AatII and a 2.9 kb long DNA fragment was isolated therefrom which contains the mgl promoter. This fragment was combined with a NcoI-AatII linker to form plasmid pBP011 (FIG. 8).

Plasmid pBP011 was cleaved with EcoRI, it was treated with Klenow DNA polymerase in order to produce blunt ends and re-cleaved with AatII. Subsequently a resulting 0.8 kb long DNA fragment with a blunt end and an AatII end which contains the mgl promoter and the linker fragment was isolated (FIG. 8).

Plasmid pBP010 was cleaved with NdeI and treated with Klenow DNA polymerase in order to produce blunt fragment ends. Subsequently these fragments were cleaved with XhoI and a 4.9 kb long fragment was isolated which contains the C-terminal region of the NMHase gene (FIG. 9).

Plasmid pBP010 was also cleaved with XhoI and AatII in the process of which a 1.5 kb long fragment could be isolated which contains the N-terminal region of the NMHase gene (FIG. 9).

Both fragments from plasmid pBP010 (4.9 kb and 1.5 kb) were ligated with the 0.8 kb fragment from pBP011 which contains the mgl promoter. The resulting plasmid was denoted pBP006 (FIG. 10) and is capable of expressing NMHase.

EXAMPLE 3

Fermentation and accumulation of recombinant NMHase in *E. coli*

*E. coli* HB101 cells (DSM 1607) were transformed with the NMHase expression plasmid pBP010. In order to ensure a better regulatability of the tac promoter the cells were additionally transformed with a plasmid which is compatible with pBP010 and which contains the lacI$^q$ gene.

The lacI$^q$ gene has already been known to one skilled in the art for a long time and is easily obtainable. pACYC 177 (DSM 3693P) or plasmids derived therefrom come into consideration as the plasmid compatible with pBP010.

3.1 Growth and preculture

2×500 ml LB medium with kanamycin and ampicillin in two 2000 ml Erlenmeyer flasks were inoculated with *E. coli* HB101/lacI$^q$/pBP010 cells. They were then incubated at 37° C. and 150 rpm (rotary shaker, Braun Certomat M). The OD at 578 nm was ca. 3.0 to 4.0 in the 10th hour at a pH of ca. 7.6.

Main fermentation

| Nutrient medium and main culture: | |
|---|---|
| glycerol 86% | 2500 g |
| lactose | |
| NH$_4$Cl | 500 g |
| MgSO$_4$ * 7 H$_2$O | 50 g |
| K$_2$HPO$_4$ | 150 g |
| casein peptone | 3000 g |
| ammonia solution 25% Merck 5432 | 500 ml |
| water | 100 l |

Fermentation course

After inoculation (1% inoculum) the culture begins to grow exponentially without delay. The temperature of the fermenter is kept at 28° C. up to an OD 578 nm of 1,400. When the desired OD is reached the temperature is decreased to 25° C., the growth slows down. In addition the oxygen transfer can be reduced. These measures are necessary in order to limit the growth and thus to counteract the formation of precipitation bodies (inclusion bodies). The correct time for the temperature shift is important, if it is carried out too soon, growth is delayed for hours, if it is carried out too late, only insoluble protein is obtained.

A further increase in activity is obtained by additionally reducing oxygen. In the fermentation with a shift in temperature the yield is ca. 2500 U/L, max 3000 U/L (150 U/OD) after 30 hours. When the amount of O$_2$ in the medium is also reduced up to 4000 U/L are obtained after 45 hours.

EXAMPLE 4

Isolation of recombinant NMHase from *E. coli*

4.1 Measurement of the enzyme activity

The determination of the enzyme activity is carried out by means of a colorimetric test which contains carbamoyl-sarcosine hydrolase, sarcosine oxidase, peroxidase, N-methylhydantoin, 4-aminoantipyrine, tribromo-3-hydroxybenzoic acid, ATP and MgCl$_2$ in phosphate buffer, pH 7.8.

Principle of the measurement

NMHase converts the N-methylhydantoin which was added to carbamoyl-sarcosine, carbamoyl-sarcosine hydrolase converts this to sarcosine, this is degraded by sarcosine oxidase to form glycine, formaldehyde and hydrogen peroxide. The peroxidase converts the added colour substrates into a dark-violet dye with the aid of the hydrogen peroxide which is formed. The increase in absorbance is measured at a wavelength of 546 nm. The enzyme test is described in detail in U.S. Pat. No. 4,816,393.

A unit (U) is defined as µmol of carbamoyl-safcosine formed per minute at 25° C. under measuring conditions in a coupled test with carbamoyl-sarcosine hydrolase, sarcosine oxidase and peroxidase. An activity of 0.16 U/ml is obtained in a 5 ml test culture. This corresponds to an increase by a factor of ca. 20 compared to the original culture (Arthrobacter spec. DSM 2563).

4.2 Enzyme purification 315 g biomass (according to Example 3) resulting from 10 l fermentation culture with a total activity of 16 KU NMHase were suspended in 2 l 0.1 mol/l potassium phosphate buffer containing 10% glycerol, pH 8.0 and lysed by treatment with lysozyme and once with 700 bar high pressure dispersion. In order to remove the nucleic acids and cell debris a 10% polyethyleneimin solution G20 (Luvalgan, MW 20000) was added until no further precipitation occurs and all the NMHase activity remained in the supernatant. For this 3% v/v G 20 solution was added at room temperature, stirred for 30 minutes and afterwards centrifuged. 8% v/v in batch wet-pressed DEAE Sephadex was added to the NMHase supernatant and after stirring for 2 hours 95% of the enzyme had been adsorbed. After filtration the exchanger was washed with phosphate buffer and the NMHase was eluted with 0.5 mol/l ammonium sulphate solution containing 0.1 mol/l K-PO₄ buffer, pH 8.0. The eluate had a specific activity of 1.1 U/mg protein. Subsequently it was heated to 55° C. for ten minutes in the presence of 50 mmol/l N-methylhydantoin (final concentration) during which interfering foreign proteins were precipitated. After centrifugation the clear supernatant was further saturated to 2.2 mol/l with ammonium sulphate and the NMHase which thereby precipitates was centrifuged down. This was followed by two crystallizations, the first crystallization takes place at a protein concentration of ca. 60 mg/ml, pH 8.0, 0.1 mol/l K-PO₄ buffer, 1.27 mol/l ammonium sulphate. Prisms form after a short time. After 24 hours the crystallization was complete, only 5% NMHase remained in the centrifuged supernatant. The NMHase crystals were dissolved in 0.1 mol/l K-PO₄ buffer and after removing undissolved constituents the enzyme solution was subjected to a second crystallization (1.05 mol/l ammonium sulphate concentration). The enzyme crystals which formed overnight were collected, resuspended in buffer, dialyzed against 20 mmol/l phosphate buffer and 2 parts raffinose were added (with respect to the amount of protein) and lyophilized. The yield was 5.8 KU NMHase=34% of the starting activity with a specific activity of 2.15 U/mg protein.

The enzyme activity was tested according to Example 4.1 after each purification step.

No catalase, creatinase, creatininase and carbamoyl-sarcosine hydrolase activities were measurable. A minimal oxidase activity (=sum of glucose oxidase, pyruvate oxidase, lactate oxidase, uricase and cholesterol oxidase) of 0.002% was noted.

The properties of the recombinant NMHase concerning the pH optimum, pH stability, temperature dependence, thermal stability, $K_M$, ATP and magnesium dependence, ammonium dependence and molecular weight corresponded to the properties of the NMHase from Arthrobacter.

EXAMPLE 5

Sequencing of the NMHase gene

Fragments from the gene coding for NMHase were subcloned into the cloning vector M13 and sequenced according to standard techniques. The nucleic acid sequence is shown in SEQ ID NO: 1. This results in a protein with 1288 amino acids whose sequence is shown in SEQ ID NO: 2.

---

We claim:
1. A reagent for the determination of the content of creatinine in liquids, comprising
   a) a protein with NMHase activity, and
   b) N-methylhydantoin at a concentration of 1 to 100 mmol per liter;
   wherein said protein with NMHase activity is produced by a process comprising
      isolating a DNA fragment containing a sequence selected from the group consisting of (1) the nucleic acid sequence shown in SEQ ID NO: 1, (2) a sequence corresponding to SEQ ID NO: 1 within the scope of the degeneracy of the genetic code, and (3) a sequence which hybridizes with SEQ ID NO: 1 or a sequence corresponding to SEQ ID NO: 1 within the scope of the degeneracy of the genetic code, under stringent conditions and which codes for a protein with N-methylhydantoinase activity;
   transforming cells with the DNA fragment;
   culturing said cells in a suitable medium; and
   isolating from the medium or the cells a protein having NMHase activity.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 3867 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..3867

( x i ) SEQUENCE DESCRIPTION: SEQ ID NO:1:

```
ATG  AAG  CGC  ATC  GGA  GTA  GAC  GTC  GGC  GGC  ACC  TTC  ACC  GAC  TTG  TAT      48
Met  Lys  Arg  Ile  Gly  Val  Asp  Val  Gly  Gly  Thr  Phe  Thr  Asp  Leu  Tyr
  1             5                  10                      15

TTT  TCG  GAC  GAT  GAC  CAG  CGC  ATC  GCT  GTG  GTC  GAG  AAG  GTT  CCC  TCG      96
Phe  Ser  Asp  Asp  Asp  Gln  Arg  Ile  Ala  Val  Val  Glu  Lys  Val  Pro  Ser
                 20                  25                      30
```

| | | | | | | | | | | | | | | | | |
|---|---|---|---|---|---|---|---|---|---|---|---|---|---|---|---|---|
| ACT | CCT | CAC | GAC | CCG | TCC | GAG | GCC | GTG | ATC | AAT | GGC | ATT | AAG | AAG | CTC | 144 |
| Thr | Pro | His 35 | Asp | Pro | Ser | Glu | Ala 40 | Val | Ile | Asn | Gly | Ile 45 | Lys | Lys | Leu | |
| TGT | GAG | AAG | GCG | GGA | GTG | TCT | CTG | TCA | GAG | ATC | GAC | CAG | CTG | GTC | CAT | 192 |
| Cys | Glu 50 | Lys | Ala | Gly | Val | Ser 55 | Leu | Ser | Glu | Ile | Asp 60 | Gln | Leu | Val | His | |
| GGG | ACT | ACG | GTA | GCC | ACC | AAC | ACC | GCA | CTA | ACG | CAC | ACT | GGC | GCG | GAA | 240 |
| Gly 65 | Thr | Thr | Val | Ala | Thr 70 | Asn | Thr | Ala | Leu | Thr 75 | His | Thr | Gly | Ala | Glu 80 | |
| GTC | GGG | ATG | ATT | ACT | ACC | GAG | GGC | TTC | CGG | GAT | ATC | TTG | CAT | ATC | GCC | 288 |
| Val | Gly | Met | Ile | Thr 85 | Thr | Glu | Gly | Phe | Arg 90 | Asp | Ile | Leu | His | Ile 95 | Ala | |
| AGG | CAC | AAA | AAA | CCG | CAT | AAT | TTC | TCT | CTG | CAG | CAG | GAT | CTG | CCG | TGG | 336 |
| Arg | His | Lys | Lys 100 | Pro | His | Asn | Phe | Ser 105 | Leu | Gln | Gln | Asp | Leu 110 | Pro | Trp | |
| CAG | ACC | AAA | CCA | CTG | ATC | AAG | CGC | CGG | TAT | CGG | CTC | ACC | GTT | AAG | GAA | 384 |
| Gln | Thr | Lys 115 | Pro | Leu | Ile | Lys | Arg 120 | Arg | Tyr | Arg | Leu | Thr 125 | Val | Lys | Glu | |
| CGT | ATC | ACC | GCG | CCG | CAC | GGT | GAG | ATC | CTG | GTC | CCT | TTG | GAT | GAG | GAT | 432 |
| Arg | Ile | Thr 130 | Ala | Pro | His | Gly | Glu 135 | Ile | Leu | Val | Pro | Leu 140 | Asp | Glu | Asp | |
| GAG | GTC | CGA | CAG | AGA | GTG | CGT | GAG | CTC | AAG | ACA | GCT | GGC | GTG | CAG | GCC | 480 |
| Glu 145 | Val | Arg | Gln | Arg | Val 150 | Arg | Glu | Leu | Lys | Thr 155 | Ala | Gly | Val | Gln | Ala 160 | |
| ATC | GCT | GTA | TGT | CTG | TTG | CAT | TCG | TAT | TTG | AAC | CCG | GAG | CAC | GAG | CAG | 528 |
| Ile | Ala | Val | Cys | Leu 165 | Leu | His | Ser | Tyr | Leu 170 | Asn | Pro | Glu | His | Glu 175 | Gln | |
| CGA | ATC | GGC | GAG | ATC | GTC | AAT | GAG | GAA | TTC | CCC | GAG | GCG | TAT | CTT | TCC | 576 |
| Arg | Ile | Gly | Glu 180 | Ile | Val | Asn | Glu | Glu 185 | Phe | Pro | Glu | Ala | Tyr 190 | Leu | Ser | |
| CTG | TCT | TCT | GAA | ATT | GTG | CCT | CTA | TAT | CGA | GAG | TAT | GAA | CGA | TTC | TCA | 624 |
| Leu | Ser | Ser 195 | Glu | Ile | Val | Pro | Leu 200 | Tyr | Arg | Glu | Tyr | Glu 205 | Arg | Phe | Ser | |
| ACT | ACC | GCA | TTA | AAT | GCC | TAC | GTT | GGC | CCT | AGG | GTC | TCG | CGC | TAC | CTG | 672 |
| Thr | Thr 210 | Ala | Leu | Asn | Ala | Tyr 215 | Val | Gly | Pro | Arg | Val 220 | Ser | Arg | Tyr | Leu | |
| CAT | CGC | CTG | CAG | GAG | CAG | GCC | GAA | AAT | TTG | GGG | TAC | CAG | CGC | GAA | ATC | 720 |
| His 225 | Arg | Leu | Gln | Glu | Gln 230 | Ala | Glu | Asn | Leu | Gly 235 | Tyr | Gln | Arg | Glu | Ile 240 | |
| CTG | CTA | ATG | CAG | TCT | TCA | GGC | GGC | ATG | GTG | CCT | ATT | GGT | GAA | GCT | GCG | 768 |
| Leu | Leu | Met | Gln | Ser 245 | Ser | Gly | Gly | Met | Val 250 | Pro | Ile | Gly | Glu | Ala 255 | Ala | |
| AAA | CGG | CCG | GTG | ACG | TTG | ATG | ATG | TCC | GGT | CCA | GTG | GGA | GGT | CTG | ATC | 816 |
| Lys | Arg | Pro | Val 260 | Thr | Leu | Met | Met | Ser 265 | Gly | Pro | Val | Gly | Gly 270 | Leu | Ile | |
| GGT | GGT | ATG | TGG | GCT | GCT | AAG | CAG | TCT | GGA | TTT | GAG | AAC | GTG | GTT | ACC | 864 |
| Gly | Gly | Met 275 | Trp | Ala | Ala | Lys | Gln 280 | Ser | Gly | Phe | Glu | Asn 285 | Val | Val | Thr | |
| CTA | GAT | ATC | GGG | GGC | ACC | TCT | GCG | GAT | ATC | GGC | GTT | GCC | TAC | CAG | GGT | 912 |
| Leu | Asp | Ile 290 | Gly | Gly | Thr | Ser | Ala 295 | Asp | Ile | Gly | Val | Ala 300 | Tyr | Gln | Gly | |
| GAG | TTG | CGC | ATG | CGC | CAC | CTG | CTG | GAC | ACG | AAG | ATC | GGT | GAT | CAT | CAA | 960 |
| Glu 305 | Leu | Arg | Met | Arg | His 310 | Leu | Leu | Asp | Thr | Lys 315 | Ile | Gly | Asp | His | Gln 320 | |
| GCC | ATG | GTT | CCC | ATG | GTG | GAT | ATC | GAC | ACT | ATC | GGT | GCC | GGC | GGC | GGT | 1008 |
| Ala | Met | Val | Pro | Met 325 | Val | Asp | Ile | Asp | Thr 330 | Ile | Gly | Ala | Gly | Gly 335 | Gly | |
| TCG | ATC | GCC | TAT | GTT | GAT | GCT | GGT | GGC | GTC | TTC | CGC | GTG | GGC | CCC | CAG | 1056 |
| Ser | Ile | Ala | Tyr | Val 340 | Asp | Ala | Gly | Gly | Val 345 | Phe | Arg | Val | Gly | Pro 350 | Gln | |
| TCA | GCT | GGT | GCT | GTT | CCG | GGG | CCG | GTC | TGT | TAC | GGC | CGC | GGT | GGA | ACG | 1104 |
| Ser | Ala | Gly | Ala | Val | Pro | Gly | Pro | Val | Cys | Tyr | Gly | Arg | Gly | Gly | Thr | |

|  |  |  |  |  |  |  |  |  |  |  |  |  |  |  |  |
|---|---|---|---|---|---|---|---|---|---|---|---|---|---|---|---|
|  |  | 355 |  |  |  |  | 360 |  |  |  |  | 365 |  |  |  |
| GAA | CCA | ACG | TCA | ACC | GAT | GCT | CAG | GTA | CTG | CTC | GGA | AGG | ATG | CGT | CCA |
| Glu | Pro | Thr | Ser | Thr | Asp | Ala | Gln | Val | Leu | Leu | Gly | Arg | Met | Arg | Pro |
|  | 370 |  |  |  | 375 |  |  |  |  | 380 |  |  |  |  |  |

1152

| GAC | AGA | ATT | CTG | GCC | GGC | TCG | GGT | TTG | GAC | ATG | GAT | CTC | GAC | CGT | GCC |
|---|---|---|---|---|---|---|---|---|---|---|---|---|---|---|---|
| Asp | Arg | Ile | Leu | Ala | Gly | Ser | Gly | Leu | Asp | Met | Asp | Leu | Asp | Arg | Ala |
| 385 |  |  |  |  | 390 |  |  |  |  | 395 |  |  |  |  | 400 |

1200

| CGC | GCT | GCC | ATG | CAA | GGA | CTG | GCC | GAC | AAG | CTC | GGC | ATG | TCC | ATC | GAA |
|---|---|---|---|---|---|---|---|---|---|---|---|---|---|---|---|
| Arg | Ala | Ala | Met | Gln | Gly | Leu | Ala | Asp | Lys | Leu | Gly | Met | Ser | Ile | Glu |
|  |  |  |  |  | 405 |  |  |  |  | 410 |  |  |  |  | 415 |

1248

| GAA | GCG | GCA | CTG | GGT | GCG | CTT | CAG | ATC | CAG | AAG | TTT | GGA | ATG | ACC | CAG |
|---|---|---|---|---|---|---|---|---|---|---|---|---|---|---|---|
| Glu | Ala | Ala | Leu | Gly | Ala | Leu | Gln | Ile | Gln | Lys | Phe | Gly | Met | Thr | Gln |
|  |  |  | 420 |  |  |  |  | 425 |  |  |  |  | 430 |  |  |

1296

| GCC | ATT | GAG | CAG | AAC | TCA | GTT | CGC | CGG | GGG | TAT | GAT | CCG | CGA | GAT | TTC |
|---|---|---|---|---|---|---|---|---|---|---|---|---|---|---|---|
| Ala | Ile | Glu | Gln | Asn | Ser | Val | Arg | Arg | Gly | Tyr | Asp | Pro | Arg | Asp | Phe |
|  |  | 435 |  |  |  |  | 440 |  |  |  |  | 445 |  |  |  |

1344

| ACT | CTT | GTC | GCT | GCC | GGT | GGA | GCT | GGC | GCC | TTG | TTC | GCC | TGT | GAG | ATT |
|---|---|---|---|---|---|---|---|---|---|---|---|---|---|---|---|
| Thr | Leu | Val | Ala | Ala | Gly | Gly | Ala | Gly | Ala | Leu | Phe | Ala | Cys | Glu | Ile |
|  | 450 |  |  |  |  | 455 |  |  |  |  | 460 |  |  |  |  |

1392

| GCT | GCT | GAA | CTC | GAA | GTG | CCG | CAC | GTA | CTG | GTC | CCG | GCT | CAT | CCA | GGC |
|---|---|---|---|---|---|---|---|---|---|---|---|---|---|---|---|
| Ala | Ala | Glu | Leu | Glu | Val | Pro | His | Val | Leu | Val | Pro | Ala | His | Pro | Gly |
| 465 |  |  |  | 470 |  |  |  |  | 475 |  |  |  |  | 480 |  |

1440

| ATC | ATC | GCA | GGT | ATC | GGG | TTG | CTG | GCC | ACG | GAT | GAG | CAA | TAC | GAG | TTT |
|---|---|---|---|---|---|---|---|---|---|---|---|---|---|---|---|
| Ile | Ile | Ala | Gly | Ile | Gly | Leu | Leu | Ala | Thr | Asp | Glu | Gln | Tyr | Glu | Phe |
|  |  |  |  | 485 |  |  |  |  | 490 |  |  |  |  | 495 |  |

1488

| GTG | GCA | ACC | AAC | CGG | TTC | AGC | TTT | GCT | TTC | CGT | GAC | GCT | GCG | GTC | ATC |
|---|---|---|---|---|---|---|---|---|---|---|---|---|---|---|---|
| Val | Ala | Thr | Asn | Arg | Phe | Ser | Phe | Ala | Phe | Arg | Asp | Ala | Ala | Val | Ile |
|  |  |  | 500 |  |  |  |  | 505 |  |  |  |  | 510 |  |  |

1536

| CAA | GCG | TCC | TAC | GAG | CAG | CTC | GAG | CGC | GAA | CGT | AAC | GCT | CAA | CTG | GAT |
|---|---|---|---|---|---|---|---|---|---|---|---|---|---|---|---|
| Gln | Ala | Ser | Tyr | Glu | Gln | Leu | Glu | Arg | Glu | Arg | Asn | Ala | Gln | Leu | Asp |
|  |  | 515 |  |  |  |  | 520 |  |  |  |  | 525 |  |  |  |

1584

| GCC | GAA | GAA | GTC | CCC | GCC | GAA | CGG | CGC | AAA | ATT | GTT | TGG | CTG | CGT | GAC |
|---|---|---|---|---|---|---|---|---|---|---|---|---|---|---|---|
| Ala | Glu | Glu | Val | Pro | Ala | Glu | Arg | Arg | Lys | Ile | Val | Trp | Leu | Arg | Asp |
|  | 530 |  |  |  |  | 535 |  |  |  |  | 540 |  |  |  |  |

1632

| GCT | CGA | TAT | GAG | GGC | CAA | GGC | TAT | GAG | ATC | CGC | TTC | GTC | GTA | CCC | GAG |
|---|---|---|---|---|---|---|---|---|---|---|---|---|---|---|---|
| Ala | Arg | Tyr | Glu | Gly | Gln | Gly | Tyr | Glu | Ile | Arg | Phe | Val | Val | Pro | Glu |
| 545 |  |  |  |  | 550 |  |  |  |  | 555 |  |  |  |  | 560 |

1680

| GGG | CCG | GTC | ACT | ACC | GCA | TGG | TTG | GAC | CAA | GCA | GAA | GCC | GCT | TTC | CAC |
|---|---|---|---|---|---|---|---|---|---|---|---|---|---|---|---|
| Gly | Pro | Val | Thr | Thr | Ala | Trp | Leu | Asp | Gln | Ala | Glu | Ala | Ala | Phe | His |
|  |  |  |  | 565 |  |  |  |  | 570 |  |  |  |  | 575 |  |

1728

| GAT | GCC | CAC | TTC | GAG | GAA | TAC | GGC | CAC | CGC | TTT | AAG | GGC | GGC | ACC | GTA |
|---|---|---|---|---|---|---|---|---|---|---|---|---|---|---|---|
| Asp | Ala | His | Phe | Glu | Glu | Tyr | Gly | His | Arg | Phe | Lys | Gly | Gly | Thr | Val |
|  |  |  | 580 |  |  |  |  | 585 |  |  |  |  | 590 |  |  |

1776

| GAG | GTG | ATC | AAT | ATC | AGG | GTG | GAA | GCC | CGT | GCC | GTT | ATG | GAT | GAA | CTG |
|---|---|---|---|---|---|---|---|---|---|---|---|---|---|---|---|
| Glu | Val | Ile | Asn | Ile | Arg | Val | Glu | Ala | Arg | Ala | Val | Met | Asp | Glu | Leu |
|  |  | 595 |  |  |  |  | 600 |  |  |  |  | 605 |  |  |  |

1824

| CCC | ACG | CCA | GAA | GCG | ACG | CAG | TCA | GGC | TCA | CTT | GAA | AAT | GCG | TTG | GTG |
|---|---|---|---|---|---|---|---|---|---|---|---|---|---|---|---|
| Pro | Thr | Pro | Glu | Ala | Thr | Gln | Ser | Gly | Ser | Leu | Glu | Asn | Ala | Leu | Val |
|  | 610 |  |  |  |  | 615 |  |  |  |  | 620 |  |  |  |  |

1872

| GAG | ACC | CGC | CCT | GTA | ACT | TTC | CAG | CAA | GCA | GGT | AAG | CCT | GTC | ACC | TTG |
|---|---|---|---|---|---|---|---|---|---|---|---|---|---|---|---|
| Glu | Thr | Arg | Pro | Val | Thr | Phe | Gln | Gln | Ala | Gly | Lys | Pro | Val | Thr | Leu |
| 625 |  |  |  |  | 630 |  |  |  |  | 635 |  |  |  |  | 640 |

1920

| GAC | ACC | GGA | TTC | TAC | GAC | CGG | GCC | AAG | ATG | GGA | ATC | GGA | ACC | ACG | TTC |
|---|---|---|---|---|---|---|---|---|---|---|---|---|---|---|---|
| Asp | Thr | Gly | Phe | Tyr | Asp | Arg | Ala | Lys | Met | Gly | Ile | Gly | Thr | Thr | Phe |
|  |  |  |  | 645 |  |  |  |  | 650 |  |  |  |  | 655 |  |

1968

| GCC | GGA | CCG | GTG | GTC | ATC | GAG | CAG | TAC | GAC | TCC | ACC | ACA | GTG | ATT | CCT |
|---|---|---|---|---|---|---|---|---|---|---|---|---|---|---|---|
| Ala | Gly | Pro | Val | Val | Ile | Glu | Gln | Tyr | Asp | Ser | Thr | Thr | Val | Ile | Pro |
|  |  | 660 |  |  |  |  | 665 |  |  |  |  | 670 |  |  |  |

2016

| CCA | GGT | TTC | ACC | GGG | ACG | GTG | GAT | GAT | GCC | GGC | AAC | CTG | GTC | ATC | GCT |
|---|---|---|---|---|---|---|---|---|---|---|---|---|---|---|---|
| Pro | Gly | Phe | Thr | Gly | Thr | Val | Asp | Asp | Ala | Gly | Asn | Leu | Val | Ile | Ala |
|  |  | 675 |  |  |  |  | 680 |  |  |  |  | 685 |  |  |  |

2064

| | | | | | | | | | | | | | | | | |
|---|---|---|---|---|---|---|---|---|---|---|---|---|---|---|---|---|
| TGC | CCA | GCG | GTC | ACC | CAG | ACT | GTG | GAG | AAG | CTG | GCC | ACC | CCG | ATT | CTC | 2112 |
| Cys | Pro 690 | Ala | Val | Thr | Gln 695 | Thr | Val | Glu | Lys | Leu | Ala | Thr 700 | Pro | Ile | Leu | |
| ATG | CGC | GTC | ATC | GGC | GGC | GCG | TTG | AAC | TCG | GCG | GCC | AAA | GAA | ATG | GCT | 2160 |
| Met 705 | Arg | Val | Ile | Gly | Gly 710 | Ala | Leu | Asn | Ser | Ala 715 | Ala | Lys | Glu | Met | Ala 720 | |
| TCG | GTG | CTT | TTC | CGC | ATG | TCT | TAC | TCA | TCG | ATC | ATC | CGC | GAA | TCG | GAG | 2208 |
| Ser | Val | Leu | Phe | Arg 725 | Met | Ser | Tyr | Ser | Ser 730 | Ile | Ile | Arg | Glu | Ser 735 | Glu | |
| GAT | CTG | GGA | GCT | GGC | CTC | TTC | GAT | AAG | GAC | GGA | AAC | GTC | CTG | GCC | GAA | 2256 |
| Asp | Leu | Gly | Ala 740 | Gly | Leu | Phe | Asp | Lys 745 | Asp | Gly | Asn | Val | Leu 750 | Ala | Glu | |
| TCA | GAT | TCC | ACC | CCA | ATG | TTC | ATG | GGC | TCC | ATG | CCG | AAA | ATT | GTC | AAA | 2304 |
| Ser | Asp | Ser 755 | Thr | Pro | Met | Phe | Met 760 | Gly | Ser | Met | Pro | Lys 765 | Ile | Val | Lys | |
| GGT | GTC | ATC | TCT | GTC | CTG | GGC | GAC | GAC | ATC | CAT | GAT | GGC | GAC | GTC | ATC | 2352 |
| Gly | Val | Ile 770 | Ser | Val | Leu | Gly | Asp 775 | Asp | Ile | His | Asp | Gly 780 | Asp | Val | Ile | |
| TTG | CAC | AAT | GAT | CCG | TAC | TTG | GGG | GCT | ACG | CAC | TCC | CCG | GAT | GTT | GCA | 2400 |
| Leu 785 | His | Asn | Asp | Pro | Tyr 790 | Leu | Gly | Ala | Thr | His 795 | Ser | Pro | Asp | Val | Ala 800 | |
| ATC | ATC | GAA | CCC | ATC | TTC | CAC | GAT | GGA | GAA | CTC | GTC | GGT | TTC | GCT | GGA | 2448 |
| Ile | Ile | Glu | Pro | Ile 805 | Phe | His | Asp | Gly | Glu 810 | Leu | Val | Gly | Phe | Ala 815 | Gly | |
| GCC | TCC | GGG | CAA | CTG | ATC | GAT | AAC | GGT | GGC | GCA | TTT | TCT | GGA | CTG | ATG | 2496 |
| Ala | Ser | Gly | Gln 820 | Leu | Ile | Asp | Asn | Gly 825 | Gly | Ala | Phe | Ser | Gly 830 | Leu | Met | |
| GTA | GAT | ATT | CAG | GAC | GTG | CAG | TCC | GAA | GGA | ACC | ATC | TTC | CGG | GCG | GTG | 2544 |
| Val | Asp | Ile 835 | Gln | Asp | Val | Gln | Ser 840 | Glu | Gly | Thr | Ile | Phe 845 | Arg | Ala | Val | |
| AAG | GTC | TAT | GAG | AAG | GGT | GTT | CGT | CAG | GAG | TCA | CTG | ATC | CGG | CAC | ATC | 2592 |
| Lys | Val | Tyr 850 | Glu | Lys | Gly | Val | Arg 855 | Gln | Glu | Ser | Leu | Ile 860 | Arg | His | Ile | |
| CTG | AAC | AAC | ACT | CGC | ACA | CCT | ACC | TCT | AAC | GAG | GGC | GAC | TTC | CAG | GCA | 2640 |
| Leu 865 | Asn | Asn | Thr | Arg | Thr 870 | Pro | Thr | Ser | Asn | Glu 875 | Gly | Asp | Phe | Gln | Ala 880 | |
| ATG | ATC | GCC | GCG | TGT | GAT | CTG | GCC | AAG | TCC | CGT | TAC | TTG | GCC | CTG | GTC | 2688 |
| Met | Ile | Ala | Ala | Cys 885 | Asp | Leu | Ala | Lys | Ser 890 | Arg | Tyr | Leu | Ala | Leu 895 | Val | |
| GAG | CGG | TAT | GGC | CGA | GAC | TCG | GTT | CGT | GAC | GCC | GGG | CAG | TTC | TGG | ATC | 2736 |
| Glu | Arg | Tyr | Gly 900 | Arg | Asp | Ser | Val | Arg 905 | Asp | Ala | Gly | Gln | Phe 910 | Trp | Ile | |
| GAT | TAT | TCA | GAG | CGT | ATC | GTA | CGC | CAG | GAA | ATC | GCT | AAG | ATT | CCG | GAT | 2784 |
| Asp | Tyr | Ser 915 | Glu | Arg | Ile | Val | Arg 920 | Gln | Glu | Ile | Ala | Lys 925 | Ile | Pro | Asp | |
| GGT | GTG | TAC | GAA | ACC | GAG | ACA | GGC | TAC | TTG | GAC | GAT | GAC | GGA | CGC | AAC | 2832 |
| Gly | Val | Tyr | Glu | Thr 930 | Glu | Thr | Gly | Tyr | Leu 935 | Asp | Asp | Asp | Gly | Arg 940 | Asn | |
| TAC | GGC | AAA | AAG | CTT | CCC | ATC | GTC | GTG | AAG | GTC | ATT | GTT | GAG | GGC | GAT | 2880 |
| Tyr | Gly 945 | Lys | Lys | Leu | Pro | Ile 950 | Val | Val | Lys | Val | Ile 955 | Val | Glu | Gly | Asp 960 | |
| GAG | ATT | ACC | TAC | GAC | CTC | ACA | GGA | TCC | TCC | GCA | CAG | GTG | CCG | ACG | GCC | 2928 |
| Glu | Ile | Thr | Tyr | Asp 965 | Leu | Thr | Gly | Ser | Ser 970 | Ala | Gln | Val | Pro | Thr 975 | Ala | |
| TAC | AAC | TGC | GCA | TTC | GAA | GGA | ACC | ACT | GTC | TCG | GCG | TTC | ACG | TTC | ATC | 2976 |
| Tyr | Asn | Cys | Ala 980 | Phe | Glu | Gly | Thr | Thr 985 | Val | Ser | Ala | Phe | Thr 990 | Phe | Ile | |
| ACC | CGC | ATG | ATG | TTC | TTG | GAT | GAG | GTC | GCG | TTC | CCG | GTA | TTC | GTC | CCA | 3024 |
| Thr | Arg | Met 995 | Met | Phe | Leu | Asp | Glu 1000 | Val | Ala | Phe | Pro | Val 1005 | Phe | Val | Pro | |
| CAG | AAC | GAG | GGC | ATG | CTC | AAA | GCG | TTG | AAG | GTG | ATC | GCA | CCG | AAG | GGA | 3072 |
| Gln | Asn | Glu | Gly | Met | Leu | Lys | Ala | Leu | Lys | Val | Ile | Ala | Pro | Lys | Gly | |

|  |  |
|---|---:|
| ACT ATC TTC AAT CCG AAC TAC CCG GCG GCT ACT TTT AGC AGA TTC TCC<br>Thr Ile Phe Asn Pro Asn Tyr Pro Ala Ala Thr Phe Ser Arg Phe Ser<br>1025                   1030                 1035                 1040 | 3120 |
| CAG GTG CAG CGT GCC GTC GAC CTA GCG TTG CGA GCG CTG GCC CCG GTC<br>Gln Val Gln Arg Ala Val Asp Leu Ala Leu Arg Ala Leu Ala Pro Val<br>                 1045                 1050                 1055 | 3168 |
| ATG CCC GAA CGA GTT ACT GCC GGA AAC TCG GCC CAT ATC CAC TTC ATG<br>Met Pro Glu Arg Val Thr Ala Gly Asn Ser Ala His Ile His Phe Met<br>            1060                 1065                 1070 | 3216 |
| TCC TAC TCT GGC TGG GAC GAA AAG CAA GGT GAG TAC TGG GTC TAT CTG<br>Ser Tyr Ser Gly Trp Asp Glu Lys Gln Gly Glu Tyr Trp Val Tyr Leu<br>               1075                 1080                 1085 | 3264 |
| GAA GTC AAT GAG GGT TCC TAT GGA GCT CGC CAG GAC TCC GAC GGC CCA<br>Glu Val Asn Glu Gly Ser Tyr Gly Ala Arg Gln Asp Ser Asp Gly Pro<br>            1090                 1095                 1100 | 3312 |
| GAT TCG GTT GAC AAC CTC ATC GCC AAC ACC CGC AAT AAT CCG ATC GAA<br>Asp Ser Val Asp Asn Leu Ile Ala Asn Thr Arg Asn Asn Pro Ile Glu<br>1105                 1110                 1115                 1120 | 3360 |
| GAA CTC GAA TGG CGG TTC CCG ATG CGT ACT GAC CGC TAC GAG CTA CGC<br>Glu Leu Glu Trp Arg Phe Pro Met Arg Thr Asp Arg Tyr Glu Leu Arg<br>               1125                 1130                 1135 | 3408 |
| GAG GAT CCG GCC GCC GCC GGC GAA TAC CGT GGC GGA ATC GGC ATT GTC<br>Glu Asp Pro Ala Ala Ala Gly Glu Tyr Arg Gly Gly Ile Gly Ile Val<br>            1140                 1145                 1150 | 3456 |
| CGG GAG AAC ACC TTC TTG GAG GAT ACT GCG GTG ACC TGC GAG GGC GAA<br>Arg Glu Asn Thr Phe Leu Glu Asp Thr Ala Val Thr Cys Glu Gly Glu<br>               1155                 1160                 1165 | 3504 |
| CGT CAC GAT TCA GAT GTC CCA TGG GGC GCC TAT GGC GGC CAC GAC GGT<br>Arg His Asp Ser Asp Val Pro Trp Gly Ala Tyr Gly Gly His Asp Gly<br>            1170                 1175                 1180 | 3552 |
| CTG AAT GCG TCC CTG ATA AAG AAC CCA GGC CGC GAC GGG GAA GAG TCC<br>Leu Asn Ala Ser Leu Ile Lys Asn Pro Gly Arg Asp Gly Glu Glu Ser<br>1185                 1190                 1195                 1200 | 3600 |
| TGG CCG TCA AAG GTC ACC GGT CGT CAG TTG CAA GCC GGT GAT TCC TTG<br>Trp Pro Ser Lys Val Thr Gly Arg Gln Leu Gln Ala Gly Asp Ser Leu<br>               1205                 1210                 1215 | 3648 |
| CAG ATC ACG GTA CCT AGC GGC GGT GGT TTC GGA GAC CCG CTC AAG CGC<br>Gln Ile Thr Val Pro Ser Gly Gly Gly Phe Gly Asp Pro Leu Lys Arg<br>            1220                 1225                 1230 | 3696 |
| AAC CCA TTG CAG GTT CTC GAA GAT GTG CTC GAT GGA TTC ACC ACC ACC<br>Asn Pro Leu Gln Val Leu Glu Asp Val Leu Asp Gly Phe Thr Thr Thr<br>               1235                 1240                 1245 | 3744 |
| GAA GCC GCT TCC AGG GAC TAC GGT GTG ATT CTC AAA ACG GTC AAT GGT<br>Glu Ala Ala Ser Arg Asp Tyr Gly Val Ile Leu Lys Thr Val Asn Gly<br>            1250                 1255                 1260 | 3792 |
| CAA CTC ACC GTC GAT CTA GCG GCC ACC GCT GTA AAA CGG GAG AAC GCA<br>Gln Leu Thr Val Asp Leu Ala Ala Thr Ala Val Lys Arg Glu Asn Ala<br>1265                 1270                 1275                 1280 | 3840 |
| GTC TCT GAG CTC AGC CAC ACC AAC TGA<br>Val Ser Glu Leu Ser His Thr Asn<br>               1285 | 3867 |

( 2 ) INFORMATION FOR SEQ ID NO:2:

( i ) SEQUENCE CHARACTERISTICS:
        ( A ) LENGTH: 1288 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

-continued

| | | | | | | | | | | | | | | |
|---|---|---|---|---|---|---|---|---|---|---|---|---|---|---|
| Met 1 | Lys | Arg | Ile | Gly 5 | Val | Asp | Val | Gly | Thr 10 | Phe | Thr | Asp | Leu | Tyr 15 |
| Phe | Ser | Asp | Asp 20 | Asp | Gln | Arg | Ile | Ala 25 | Val | Val | Glu | Lys | Val 30 | Pro | Ser |
| Thr | Pro | His 35 | Asp | Pro | Ser | Glu | Ala 40 | Val | Ile | Asn | Gly | Ile 45 | Lys | Lys | Leu |
| Cys | Glu 50 | Lys | Ala | Gly | Val | Ser 55 | Leu | Ser | Glu | Ile | Asp 60 | Gln | Leu | Val | His |
| Gly 65 | Thr | Thr | Val | Ala | Thr 70 | Asn | Thr | Ala | Leu | Thr 75 | His | Thr | Gly | Ala | Glu 80 |
| Val | Gly | Met | Ile | Thr 85 | Thr | Glu | Gly | Phe | Arg 90 | Asp | Ile | Leu | His | Ile 95 | Ala |
| Arg | His | Lys | Lys 100 | Pro | His | Asn | Phe | Ser 105 | Leu | Gln | Gln | Asp | Leu 110 | Pro | Trp |
| Gln | Thr | Lys 115 | Pro | Leu | Ile | Lys | Arg 120 | Arg | Tyr | Arg | Leu | Thr 125 | Val | Lys | Glu |
| Arg | Ile 130 | Thr | Ala | Pro | His | Gly 135 | Glu | Ile | Leu | Val | Pro 140 | Leu | Asp | Glu | Asp |
| Glu 145 | Val | Arg | Gln | Arg | Val 150 | Arg | Glu | Leu | Lys | Thr 155 | Ala | Gly | Val | Gln | Ala 160 |
| Ile | Ala | Val | Cys | Leu 165 | Leu | His | Ser | Tyr | Leu 170 | Asn | Pro | Glu | His | Glu 175 | Gln |
| Arg | Ile | Gly | Glu 180 | Ile | Val | Asn | Glu | Glu 185 | Phe | Pro | Glu | Ala | Tyr 190 | Leu | Ser |
| Leu | Ser | Ser 195 | Glu | Ile | Val | Pro | Leu 200 | Tyr | Arg | Glu | Tyr | Glu 205 | Arg | Phe | Ser |
| Thr 210 | Thr | Ala | Leu | Asn | Ala 215 | Tyr | Val | Gly | Pro | Arg 220 | Val | Ser | Arg | Tyr | Leu |
| His 225 | Arg | Leu | Gln | Glu | Gln 230 | Ala | Glu | Asn | Leu | Gly 235 | Tyr | Gln | Arg | Glu | Ile 240 |
| Leu | Leu | Met | Gln | Ser 245 | Ser | Gly | Gly | Met | Val 250 | Pro | Ile | Gly | Glu | Ala 255 | Ala |
| Lys | Arg | Pro | Val 260 | Thr | Leu | Met | Met | Ser 265 | Gly | Pro | Val | Gly | Gly 270 | Leu | Ile |
| Gly | Gly | Met 275 | Trp | Ala | Ala | Lys | Gln 280 | Ser | Gly | Phe | Glu | Asn 285 | Val | Val | Thr |
| Leu | Asp 290 | Ile | Gly | Gly | Thr | Ser 295 | Ala | Asp | Ile | Gly | Val 300 | Ala | Tyr | Gln | Gly |
| Glu 305 | Leu | Arg | Met | Arg | His 310 | Leu | Leu | Asp | Thr | Lys 315 | Ile | Gly | Asp | His | Gln 320 |
| Ala | Met | Val | Pro | Met 325 | Val | Asp | Ile | Asp | Thr 330 | Ile | Gly | Ala | Gly | Gly 335 | Gly |
| Ser | Ile | Ala | Tyr 340 | Val | Asp | Ala | Gly | Gly 345 | Val | Phe | Arg | Val | Gly 350 | Pro | Gln |
| Ser | Ala | Gly 355 | Ala | Val | Pro | Gly | Pro 360 | Val | Cys | Tyr | Gly | Arg 365 | Gly | Gly | Thr |
| Glu | Pro 370 | Thr | Ser | Thr | Asp | Ala 375 | Gln | Val | Leu | Leu | Gly 380 | Arg | Met | Arg | Pro |
| Asp 385 | Arg | Ile | Leu | Ala | Gly 390 | Ser | Gly | Leu | Asp | Met 395 | Asp | Leu | Asp | Arg | Ala 400 |
| Arg | Ala | Ala | Met | Gln 405 | Gly | Leu | Ala | Asp | Lys 410 | Leu | Gly | Met | Ser | Ile 415 | Glu |
| Glu | Ala | Ala | Leu 420 | Gly | Ala | Leu | Gln | Ile 425 | Gln | Lys | Phe | Gly | Met 430 | Thr | Gln |
| Ala | Ile | Glu | Gln | Asn | Ser | Val | Arg | Arg | Gly | Tyr | Asp | Pro | Arg | Asp | Phe |

|     |     |     |     |     | 435 |     |     |     |     | 440 |     |     |     |     | 445 |     |     |
| --- | --- | --- | --- | --- | --- | --- | --- | --- | --- | --- | --- | --- | --- | --- | --- | --- | --- |
| Thr | Leu | Val | Ala | Ala | Gly | Gly | Ala | Gly | Ala | Leu | Phe | Ala | Cys | Glu | Ile |
|     | 450 |     |     |     |     | 455 |     |     |     |     | 460 |     |     |     |     |
| Ala | Ala | Glu | Leu | Glu | Val | Pro | His | Val | Leu | Val | Pro | Ala | His | Pro | Gly |
| 465 |     |     |     |     | 470 |     |     |     |     | 475 |     |     |     |     | 480 |
| Ile | Ile | Ala | Gly | Ile | Gly | Leu | Leu | Ala | Thr | Asp | Glu | Gln | Tyr | Glu | Phe |
|     |     |     |     | 485 |     |     |     |     | 490 |     |     |     |     | 495 |     |
| Val | Ala | Thr | Asn | Arg | Phe | Ser | Phe | Ala | Phe | Arg | Asp | Ala | Ala | Val | Ile |
|     |     |     | 500 |     |     |     |     | 505 |     |     |     | 510 |     |     |     |
| Gln | Ala | Ser | Tyr | Glu | Gln | Leu | Glu | Arg | Glu | Arg | Asn | Ala | Gln | Leu | Asp |
|     |     | 515 |     |     |     |     | 520 |     |     |     |     | 525 |     |     |     |
| Ala | Glu | Glu | Val | Pro | Ala | Glu | Arg | Arg | Lys | Ile | Val | Trp | Leu | Arg | Asp |
| 530 |     |     |     |     |     | 535 |     |     |     |     | 540 |     |     |     |     |
| Ala | Arg | Tyr | Glu | Gly | Gln | Gly | Tyr | Glu | Ile | Arg | Phe | Val | Val | Pro | Glu |
| 545 |     |     |     |     | 550 |     |     |     |     | 555 |     |     |     |     | 560 |
| Gly | Pro | Val | Thr | Thr | Ala | Trp | Leu | Asp | Gln | Ala | Glu | Ala | Ala | Phe | His |
|     |     |     |     | 565 |     |     |     |     | 570 |     |     |     |     | 575 |     |
| Asp | Ala | His | Phe | Glu | Glu | Tyr | Gly | His | Arg | Phe | Lys | Gly | Gly | Thr | Val |
|     |     |     | 580 |     |     |     |     | 585 |     |     |     |     | 590 |     |     |
| Glu | Val | Ile | Asn | Ile | Arg | Val | Glu | Ala | Arg | Ala | Val | Met | Asp | Glu | Leu |
|     |     |     | 595 |     |     |     |     | 600 |     |     |     |     | 605 |     |     |
| Pro | Thr | Pro | Glu | Ala | Thr | Gln | Ser | Gly | Ser | Leu | Glu | Asn | Ala | Leu | Val |
|     | 610 |     |     |     |     | 615 |     |     |     |     | 620 |     |     |     |     |
| Glu | Thr | Arg | Pro | Val | Thr | Phe | Gln | Gln | Ala | Gly | Lys | Pro | Val | Thr | Leu |
| 625 |     |     |     |     | 630 |     |     |     |     | 635 |     |     |     |     | 640 |
| Asp | Thr | Gly | Phe | Tyr | Asp | Arg | Ala | Lys | Met | Gly | Ile | Gly | Thr | Thr | Phe |
|     |     |     |     | 645 |     |     |     |     | 650 |     |     |     |     | 655 |     |
| Ala | Gly | Pro | Val | Val | Ile | Glu | Gln | Tyr | Asp | Ser | Thr | Thr | Val | Ile | Pro |
|     |     |     | 660 |     |     |     |     | 665 |     |     |     |     | 670 |     |     |
| Pro | Gly | Phe | Thr | Gly | Thr | Val | Asp | Asp | Ala | Gly | Asn | Leu | Val | Ile | Ala |
|     |     | 675 |     |     |     |     | 680 |     |     |     |     | 685 |     |     |     |
| Cys | Pro | Ala | Val | Thr | Gln | Thr | Val | Glu | Lys | Leu | Ala | Thr | Pro | Ile | Leu |
|     | 690 |     |     |     |     | 695 |     |     |     |     | 700 |     |     |     |     |
| Met | Arg | Val | Ile | Gly | Gly | Ala | Leu | Asn | Ser | Ala | Ala | Lys | Glu | Met | Ala |
| 705 |     |     |     |     | 710 |     |     |     |     | 715 |     |     |     |     | 720 |
| Ser | Val | Leu | Phe | Arg | Met | Ser | Tyr | Ser | Ser | Ile | Ile | Arg | Glu | Ser | Glu |
|     |     |     |     | 725 |     |     |     |     | 730 |     |     |     |     | 735 |     |
| Asp | Leu | Gly | Ala | Gly | Leu | Phe | Asp | Lys | Asp | Gly | Asn | Val | Leu | Ala | Glu |
|     |     |     | 740 |     |     |     |     | 745 |     |     |     |     | 750 |     |     |
| Ser | Asp | Ser | Thr | Pro | Met | Phe | Met | Gly | Ser | Met | Pro | Lys | Ile | Val | Lys |
|     |     | 755 |     |     |     |     | 760 |     |     |     |     | 765 |     |     |     |
| Gly | Val | Ile | Ser | Val | Leu | Gly | Asp | Asp | Ile | His | Asp | Gly | Asp | Val | Ile |
|     | 770 |     |     |     |     | 775 |     |     |     |     | 780 |     |     |     |     |
| Leu | His | Asn | Asp | Pro | Tyr | Leu | Gly | Ala | Thr | His | Ser | Pro | Asp | Val | Ala |
| 785 |     |     |     |     | 790 |     |     |     |     | 795 |     |     |     |     | 800 |
| Ile | Ile | Glu | Pro | Ile | Phe | His | Asp | Gly | Glu | Leu | Val | Gly | Phe | Ala | Gly |
|     |     |     |     | 805 |     |     |     |     | 810 |     |     |     |     | 815 |     |
| Ala | Ser | Gly | Gln | Leu | Ile | Asp | Asn | Gly | Gly | Ala | Phe | Ser | Gly | Leu | Met |
|     |     |     | 820 |     |     |     |     | 825 |     |     |     |     | 830 |     |     |
| Val | Asp | Ile | Gln | Asp | Val | Gln | Ser | Glu | Gly | Thr | Ile | Phe | Arg | Ala | Val |
|     |     | 835 |     |     |     |     | 840 |     |     |     |     | 845 |     |     |     |
| Lys | Val | Tyr | Glu | Lys | Gly | Val | Arg | Gln | Glu | Ser | Leu | Ile | Arg | His | Ile |
|     | 850 |     |     |     |     | 855 |     |     |     |     | 860 |     |     |     |     |
| Leu | Asn | Asn | Thr | Arg | Thr | Pro | Thr | Ser | Asn | Glu | Gly | Asp | Phe | Gln | Ala |
| 865 |     |     |     |     | 870 |     |     |     |     | 875 |     |     |     |     | 880 |

```
Met  Ile  Ala  Ala  Cys  Asp  Leu  Ala  Lys  Ser  Arg  Tyr  Leu  Ala  Leu  Val
               885                     890                     895

Glu  Arg  Tyr  Gly  Arg  Asp  Ser  Val  Arg  Asp  Ala  Gly  Gln  Phe  Trp  Ile
          900                     905                     910

Asp  Tyr  Ser  Glu  Arg  Ile  Val  Arg  Gln  Glu  Ile  Ala  Lys  Ile  Pro  Asp
     915                     920                     925

Gly  Val  Tyr  Glu  Thr  Glu  Thr  Gly  Tyr  Leu  Asp  Asp  Asp  Gly  Arg  Asn
930                      935                    940

Tyr  Gly  Lys  Lys  Leu  Pro  Ile  Val  Val  Lys  Val  Ile  Val  Glu  Gly  Asp
945                      950                    955                         960

Glu  Ile  Thr  Tyr  Asp  Leu  Thr  Gly  Ser  Ser  Ala  Gln  Val  Pro  Thr  Ala
               965                     970                     975

Tyr  Asn  Cys  Ala  Phe  Glu  Gly  Thr  Thr  Val  Ser  Ala  Phe  Thr  Phe  Ile
          980                     985                     990

Thr  Arg  Met  Met  Phe  Leu  Asp  Glu  Val  Ala  Phe  Pro  Val  Phe  Val  Pro
          995                    1000                    1005

Gln  Asn  Glu  Gly  Met  Leu  Lys  Ala  Leu  Lys  Val  Ile  Ala  Pro  Lys  Gly
          1010                   1015                   1020

Thr  Ile  Phe  Asn  Pro  Asn  Tyr  Pro  Ala  Ala  Thr  Phe  Ser  Arg  Phe  Ser
1025                     1030                   1035                        1040

Gln  Val  Gln  Arg  Ala  Val  Asp  Leu  Ala  Leu  Arg  Ala  Leu  Ala  Pro  Val
               1045                    1050                    1055

Met  Pro  Glu  Arg  Val  Thr  Ala  Gly  Asn  Ser  Ala  His  Ile  His  Phe  Met
          1060                    1065                    1070

Ser  Tyr  Ser  Gly  Trp  Asp  Glu  Lys  Gln  Gly  Glu  Tyr  Trp  Val  Tyr  Leu
          1075                    1080                    1085

Glu  Val  Asn  Glu  Gly  Ser  Tyr  Gly  Ala  Arg  Gln  Asp  Ser  Asp  Gly  Pro
1090                     1095                   1100

Asp  Ser  Val  Asp  Asn  Leu  Ile  Ala  Asn  Thr  Arg  Asn  Asn  Pro  Ile  Glu
1105                     1110                   1115                        1120

Glu  Leu  Glu  Trp  Arg  Phe  Pro  Met  Arg  Thr  Asp  Arg  Tyr  Glu  Leu  Arg
               1125                    1130                    1135

Glu  Asp  Pro  Ala  Ala  Ala  Gly  Glu  Tyr  Arg  Gly  Gly  Ile  Gly  Ile  Val
          1140                    1145                    1150

Arg  Glu  Asn  Thr  Phe  Leu  Glu  Asp  Thr  Ala  Val  Thr  Cys  Glu  Gly  Glu
          1155                    1160                    1165

Arg  His  Asp  Ser  Asp  Val  Pro  Trp  Gly  Ala  Tyr  Gly  Gly  His  Asp  Gly
          1170                    1175                    1180

Leu  Asn  Ala  Ser  Leu  Ile  Lys  Asn  Pro  Gly  Arg  Asp  Gly  Glu  Glu  Ser
1185                     1190                   1195                        1200

Trp  Pro  Ser  Lys  Val  Thr  Gly  Arg  Gln  Leu  Gln  Ala  Gly  Asp  Ser  Leu
               1205                    1210                    1215

Gln  Ile  Thr  Val  Pro  Ser  Gly  Gly  Gly  Phe  Gly  Asp  Pro  Leu  Lys  Arg
               1220                    1225                    1230

Asn  Pro  Leu  Gln  Val  Leu  Glu  Asp  Val  Leu  Asp  Gly  Phe  Thr  Thr  Thr
               1235                    1240                    1245

Glu  Ala  Ala  Ser  Arg  Asp  Tyr  Gly  Val  Ile  Leu  Lys  Thr  Val  Asn  Gly
          1250                    1255                    1260

Gln  Leu  Thr  Val  Asp  Leu  Ala  Ala  Thr  Ala  Val  Lys  Arg  Glu  Asn  Ala
1265                     1270                   1275                        1280

Val  Ser  Glu  Leu  Ser  His  Thr  Asn
                    1285
```

( 2 ) INFORMATION FOR SEQ ID NO:3:

(i) SEQUENCE CHARACTERISTICS:
    (A) LENGTH: 17 amino acids
    (B) TYPE: amino acid
    (D) TOPOLOGY: linear (xi) SEQUENCE DESCRIPTION: SEQ ID NO:3:

Met Lys Arg Ile Gly Val Asp Val Gly Gly Thr Phe Thr Asp Leu Tyr
 1               5                  10                  15
Phe (2) INFORMATION FOR SEQ ID NO:4:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:4:

ATGAARMGRA THGGNGT                                              17

(2) INFORMATION FOR SEQ ID NO:5:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:5:

ATGAARMGYA THGGNGT                                              17

(2) INFORMATION FOR SEQ ID NO:6:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO:6:

ATGAAGCGCA TCGGCGTGGA CGTGGGCGGC ACGTTCACCG ATCTGTACTT           50